United States Patent [19]

Schmitt et al.

[11] Patent Number: 4,649,281

[45] Date of Patent: Mar. 10, 1987

[54] OIL CONTENT MONITOR/CONTROL SYSTEM

[75] Inventors: Ray F. Schmitt, Riviera Beach; Joseph A. Gavin, Glen Burnie; Francis D. Kempel, Sudlersville, all of Md.; Charles N. Waltrick, deceased, late of Glen Burnie, Md., by Steven B. Waltrick, Cathy M. Waltrick, legal representatives

[73] Assignee: The United States of America as represented by the Secretary of the Navy, Washington, D.C.

[21] Appl. No.: 751,346

[22] Filed: Jul. 2, 1985

[51] Int. Cl.$^4$ ............... G01N 21/49; B01D 17/04; C02F 1/40

[52] U.S. Cl. .................. 250/574; 137/172; 210/96.1; 210/85; 210/167; 210/194; 210/DIG. 5

[58] Field of Search ............. 210/96.1, 194, 167, 210/85, DIG. 5; 141/83, 130, 98; 137/172; 250/573-576

[56] References Cited

U.S. PATENT DOCUMENTS

| | | | |
|---|---|---|---|
| 3,253,711 | 5/1966 | Young | 137/172 |
| 3,787,703 | 1/1974 | Topol | 250/574 |
| 3,965,004 | 6/1976 | Garber | 210/DIG. 5 |
| 3,966,603 | 6/1976 | Grant | 210/DIG. 5 |
| 4,064,893 | 12/1977 | Pitt | 210/96.1 |
| 4,265,535 | 5/1981 | Pitt | 250/574 |
| 4,315,822 | 2/1982 | Jaisinghani | 210/96.1 |
| 4,344,429 | 8/1982 | Gupton et al. | 250/574 |

Primary Examiner—Edward P. Westin
Attorney, Agent, or Firm—Kenneth E. Walden; John G. Wynn

[57] ABSTRACT

An oil content monitor/control unit system is configured to automatically monitor and control processed effluent from an associated oil/water separator so that if the processed effluent exceeds predetermined in-port or at-sea oil concentration limits, it is either recirculated to an associated oil/water separator via a ship's bilge for additional processing, or diverted to a holding tank for storage. On the other hand, if the oil concentration of the processed effluent is less than predetermined in-port or at-sea limits, it is discharged overboard.

4 Claims, 3 Drawing Figures

OIL CONTENT MONITOR/CONTROL SYSTEM

CROSS-REFERENCE TO RELATED APPLICATION

The present application contains subject matter which is related to the subject matter disclosed in U.S. patent application Ser. No. 751,346, to Ray F. Schmitt, et al, entitled, "An Oil/Water Disperser Device For Use In An Oil Content Monitor/Control System", filed July 2, 1985, and assigned to the same assignee as the present application.

BACKGROUND OF THE INVENTION

1. Field of the Invention

The present invention relates to oil-in-water concentration detecting and measuring systems and methods in general, but more specifically, it relates to an oil content monitor/control system which automatically monitors and controls processed effluent from an associated shipboard oil/water separator.

2. Description of the Prior Art

The Navy has been engaged in a research and development effort to provide the fleet with shipboard oily waste treatment systems to satisfy certain advanced development objectives. The Navy's oily waste advanced development objectives reflect international pollution control standards pertaining to the operation of ships promulgated by the Internatinal Maritime Organization (IMO), of which the United States is a signatory. The IMO oily waste overboard discharge standards are 15 parts per million (ppm) oil maximum in-port (within 50 miles of shore) and 100 ppm oil maximum at-sea. An essential element of the Navy's effort is the development of accurate and reliable oil content monitor systems to examine the quality of processed effluents from shipboard oil/water separators and to ensure that the oily waste overboard discharge objectives are met.

Several of the prior art systems have been evaluated both in the laboratory and aboard ship. Most of these systems have design shortcomings which adversely effect system accuracy, reliability, and maintainability.

As further background material, in U.S. Pat. No. 3,787,703 to Topol, entitled, "Optical Sensing Sampling Head", and filed May 25, 1972, is disclosed an optical sensing head configured for use with a probe to be immersed in a fluid. The sensing head probe combination operates to detect direct, and refract light transmission characteristics of the fluid and provide electrical signals representative thereof for further use and or analysis. The disclosure of Topol is incorporated herein by reference.

As still further background material, in U.S. Pat. No. 4,265,535, to Pitt, entitled, "Oil/In Water Method and Detector", filed Apr. 25, 1979, is disclosed a light scattering oil-in-water detector and a clean/dirty ballast monitoring system for use therewith. A light beam is directed into water having oil dispersed therein, and scattered light is measured at a plurality of angles with respect to the incident light beam, one of the measurements being made at an angle at which substantially no light is scattered by the oil.

The prior art, as indicated hereinabove include advances in oil content monitor/control systems and methods. However, insofar as can be determined, no prior art system or method incorporates all of the features and advantages of the present invention.

OBJECTS OF THE INVENTION

Accordingly, a principal object of the present invention is to automatically monitor and control processed effluent from an associated shipboard oil/water separator so that if it exceeds predetermined in-port or at-sea levels, it is either recirculated to an associated ship's bilge for additional processing, or diverted to a holding tank for storage.

A corollary object of the foregoing object is to discharge the processed effluent overboard if it is less than the predetermined in-port or in-sea levels.

Another object of the present invention is to incorporate into the design of the oil content monitor/control system an oil/water disperser device to break up the oil present in the processed effluent into uniform small droplets so that the oil-in-water concentration can be measured more accurately.

Yet another object of the present invention is to incorporate into the oil content monitor/control system visual and audible alarm indicators that will be actuated when the predetermined oil-in-water concentration levels are exceeded.

Still a further object of the present invention is to include therein an alarm delay so as to prevent a momentary slug of excessively oily processed effluent from triggering the alarm.

SUMMARY OF THE INVENTION

In accordance with the above stated objects, other objects, features and advantages, the present invention has as a primary purpose to automatically monitor and control processed effluent from an associated oil/water separator.

The essence of the present invention lies in its ability to control the effluent if it exceeds preset in/port or at/sea oil concentration limits, i.e., either recirculate the processed effluent to a ship's bilge for additional processing, divert it to a holding tank for storage or discharge it overboard according to predetermined in-port or at-sea oil concentration limits.

The purpose of the present invention is carried-out by configuring the oil content monitor/control system to comprise, inter alia, an oil/water disperser device for uniformly distributing the oil present in the processed effluent into small droplets, a sensing/sampling probe device for sampling the processed effluent so as to determine the intensity of scattered and transmitted light, and in response thereto providing an electrical signal corresponding to the oil-in-water concentration, and a monitor/control device for displaying the level of oil-in-water concentration of the processed effluent, and for either causing the processed effluent to be recirculated to the ship's bilge for additional processing, diverted to the holding tank for storage, or discharged overboard.

BRIEF DESCRIPTION OF THE DRAWINGS

The previously stated objects, other objects, features and advantages of the present invention will be apparent from the following more particular description of a preferred embodiment as illustrated in the accompanying drawings, in which.

DESCRIPTION OF THE PREFERRED EMBODIMENT

Figure 1:
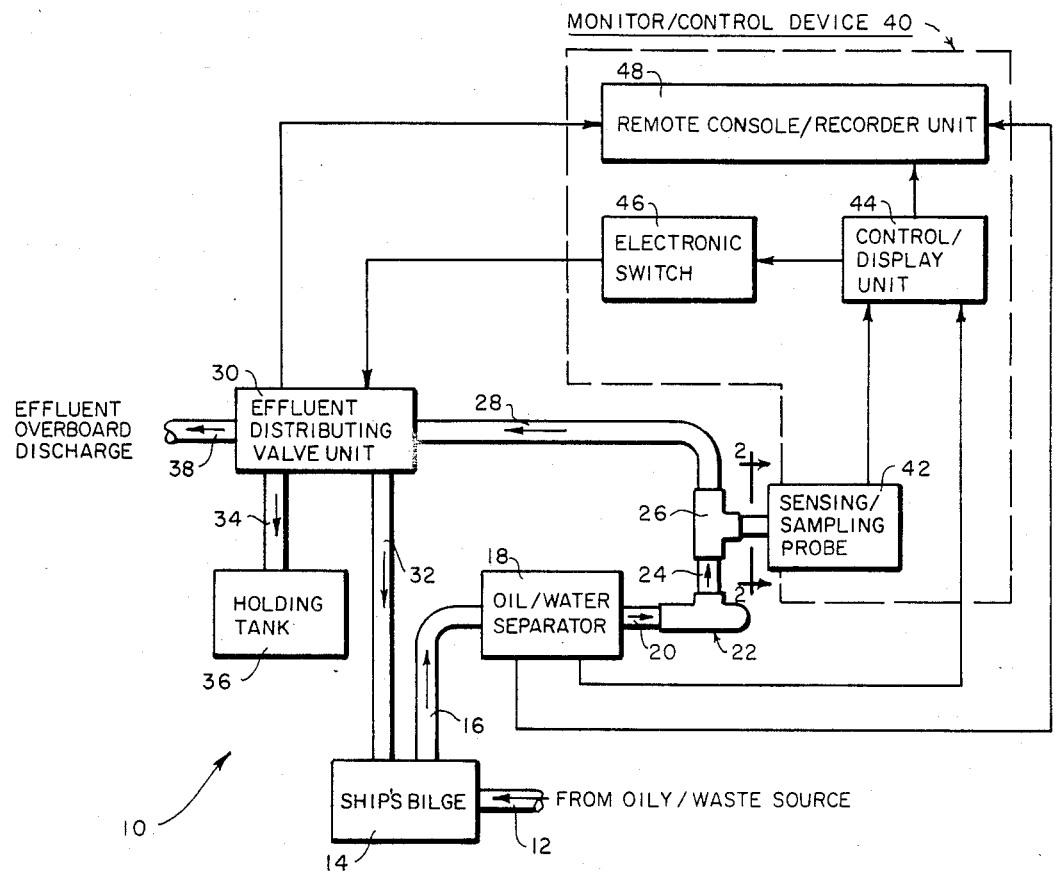
FIG. 1 is a block diagram representation of the oil content monitor/control system, according to the present invention, including, inter alia, a disperser device, a sensing/sampling probe and an oil/water separator according to the present invention.

FIG. 1 shows an embodiment of an oil content monitor/control system 10 in which the present invention is employed to automatically monitor and control processed effluent according to predetermined oil-in-water concentration limits. Contaminated effluent, from an oily/waste source, via an effluent pipe section 12, flows into a ship's bilge 14 where, via an influent pipe section 16, it enters an associated oil/water separator 18. For purposes of the present invention, the oil/water separator 18 can be a General Electric Model OPB-10N system which has a 10 gallon per minute (gpm) throughput. To continue, after the oil is separated from the water in oil/water separator 18, the processed effluent, via an effluent pipe section 20, enters an oil/water disperser device 22 where any oil left in the processed effluent is broken up into uniform small droplets. The processed effluent, now containing a uniform distribution of oil droplets, flows, via an effluent pipe section 24, into an effluent tee connector 26, and out of the effluent tee connector 26, via an effluent pipe section 24, into an effluent distributing valve unit 30. The effluent distributing valve unit 30 distributes the processed effluent, via an effluent pipe section 32, back to the ship's bilge 14 for recirculation and further processing; via an effluent pipe section 34, into a holding tank 36 for storage; or, via an effluent pipe 38, overboard according to the oil-in-water predetermined concentration limits chosen.

Still referring to the block diagram representation of FIG. 1, the oil content monitor/control system 10 further comprises a monitor/control device 40 for, inter alia, automatically monitoring and controlling the recirculation, storage, or discharge overboard of the processed effluent, via the effluent distributing valve unit 30. A more detailed description of some aspects of the monitor/control device 40 and operation of the complete oil content monitor/control system 10 will be described hereinafter under the heading "Statement of the Operation". Continuing, the monitor/control device 40 comprises a sensing/sampling probe 42 which is operatively connected to the aforementioned effluent tee connector 26 for sampling the processed effluent and measuring the oil-in-water concentration thereof. The output of the sensing/sampling probe 42 comprises electrical signals indicative of the oil-in-water concentration of the processed effluent. These electrical signals feed a control/display unit 44 which, inter alia, provides a visual display of the oil-in-water concentration levels on a meter (not shown). The control/display unit 44 contains the logic for controlling an electronic switch 46. The control/display unit 44 also provides oil-in-water concentration level information to the remote console/recorder unit 48. The electronic switch 46 in coaction with the control unit 44 controls the distribution operation of the effluent distributing valve unit 30. Status information from the effluent distributing valve unit 30 is fed back to the remote console/recorder unit 48 for a continuous indication of the operation thereof.

In addition, control and status signals from the oil/water separator 18 are fed to the control/display unit 44 and the remote console/recorder unit 48 on separate status lines as shown. The oil content monitor/control system includes a sensing/sampling probe 42 operatively connected at its input to the output of oil/water disperser 22 device for accurately measuring the oil-in-water concentration level of the processed effluent. Sensing/sampling probe 42 operates to extract a sample of the processed effluent including uniform small droplets of oil. The sample is examined optically for scattered and transmitted light. A ratio of electrical signals proportional to the ratio of scattered light and transmitted light, respectively, through the sample is proportional to the oil-in-water concentration level of the processed effluent. A control/display unit 44 is operatively connected to the output of the sensing/sampling probe and to the oil/water separator 18. Control/display unit 44 is configured to display the oil-in-water concentration level of the processed effluent and provide a control signal representative of the oil-in-water concentration level of the processed effluent.

STATEMENT OF THE OPERATION

Figure 2:
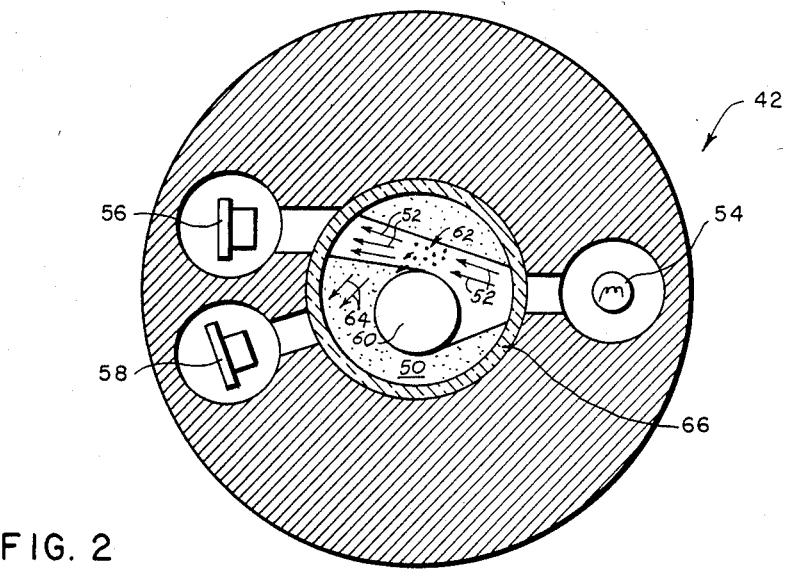
FIG. 2 is a cross-sectional view of the sensing/sampling probe of FIG. 1 taken along lines 2—2 thereof, according to the present invention.

Details of the operation, according to the present invention, are explained in conjunction with FIGS. 1 and 2 as viewed concurrently.

In operation, the oil/water disperser device 22 is located downstream of the oil/water separator 18 and upstream of the sensing/sampling probe 42 within 1 to 4 feet of the sensing/sampling probe 42. The oil/water disperser 22 breaks up the oil present in the processed effluent into uniform small droplets so that the sensing/sampling probe 42 can measure the oil-in-water concentration therein accurately.

Still referring to FIGS. 1 and 2, as viewed concurrently, the sensing/sampling probe 42 extracts a processed effluent sample, examines the sample optically for scattered and transmitted light, and provides an electrical signal to the control/display unit 44 for visual display of oil-in-water concentration levels. The sensing/sampling probe 42 is flange-mounted (not shown) to the effluent tee connector 26, which is vertically mounted to the aforementioned effluent pipe sections 24 and 28, as shown. An optical sensing and sampling probe suitable for use as the sensing/sampling probe 42 is disclosed in the U.S. patent to Topol previously cited in the "Background of the Invention" section of the present application. As previously mentioned, the teachings of Topol are incorporated herein by reference. However, to better understand the specific nature of the light paths involved in the sensing/sampling process, specific reference should be made to FIG. 2, which is a cross-sectional view of the sensing/sampling probe 42 taken along lines 2—2 of FIG. 1. (It should be noted that FIG. 2 is substantially the same as FIG. 5 of Topol, but with different reference numbers.)

As shown in FIG. 2, the chamber 50 is formed, as taught in Topol, by withdrawing a piston (not shown). As indicated by arrows 52, light is transmitted directly from a light source 54 to a transmit photocell 56. If the processed effluent contained in the chamber 50 is perfectly clear, a scatter photocell 58 would be completely in the shadow of occluding rod 60, and, accordingly, would not receive any light. However, if the processed effluent drawn into the chamber 50 contains dispersed oil droplets 62, scattered or reflected light is directed toward the scatter photocell 58, as indicated by arrows 64. Consequently, the light level received at the scatter photocell 58 is a measure of the contamination of the processed effluent. Thus, when oil droplets are present, the intensity of the transmitted light is reduced, and the intensity of the scattered light increases with an inherent correction for changing characteristics of the light source 54 and the transparency characteristics of the glass tube 66. The oil-in-water concentration, then, is proportional to the ratio of the scattered light to the transmitted light. This ratio of the electrical signals from the transmit photocell 56 and the scatter photocell 58 is determined by electronic circuitry (not shown) in the sensing/sampling probe 42.

Continuing, the foregoing ratio is converted to a voltage and fed to the control/display unit 44 where a meter (not shown) provide a continuous readout of the oil-in-water concentration levels in parts per million (ppm) as long as the oil content monitor/control system 10 of FIG. 1 is in an "on-line" operating mode. The piston (not shown) of the sensing/sampling probe 42 extracts a sample of the processed effluent every 8.5 seconds. If the processed effluent exceeds in-port or at-sea concentration limits, which are preset in the control/display unit 44, an alarm condition is indicated at the remote console/recorder unit 48. As shown in FIG. 1, the processed effluent is then either recirculated to the ship's bilge 14 for additional processing, diverted to the holding tank 36 for storage, or discharged overboard if the concentration level is within the predetermined levels. When the concentration level of the processed effluent returns to a no-alarm condition for 8 seconds, overboard discharge resumes.

Still referring to FIGS. 1 and 2 as viewed concurrently, when the oil/water separator 18 is not operating, the oil content monitor/control system 10 is in the "stand-by" mode as sensed on the two status lines, aforementioned. The oil content monitor/control system 10 is configured to be in "stand-by" continuously. In the "stand-by" mode, the piston (not shown) for sampling in the sensing/sampling probe 42 is in the full forward position to keep contaminants, such as rust and dirt, from fouling the chamber 50. When the oil/water separator 18 starts processing oily/waste, the oil content monitor/control system 10 begins sampling and monitoring automatically in the "on-line" operational mode.

The control/display unit 44 contains the logic which controls the operation of the oil content monitor/control system 10. In addition, the control/display unit 44 comprises the meter which displays oil-in-water concentration, lights which indicate the operating status of the oil content monitor/control system 10, and switches by which an operator can control operation of the system. For purposes of the present invention, the meter is a direct reading, light emitting diode (LED) type unit. It has an in-port, ("Low Range") scale calibrated from 0 to 30 ppm and an at-sea ("Hi Range") scale calibrated from 0 to 150 ppm. The predetermined in-port and at-sea concentration limits are 15 ppm and 100 ppm, respectively.

A signal from the control/display unit 44, predicated on the concentration levels previously determined, drives the electronic switch 46. For purposes of the present invention, the electronic switch 46 can be a solid state relay whose contacts control a voltage source, for example 110 volts, for driving the effluent distributing valve unit 30 at the proper time. Also, for purposes of the present invention the effluent distributing valve unit 30 can be an electronically-actuated solenoid valve.

In addition to the alarm condition indication, the remote console/recorder unit 48 provides illuminated indications of the status of the oil/water separator 18 and the oil content monitor/control system 10 and the effluent distributing valve unit 30. It also via its recorder portion (not shown), registers the processed effluent oil-in-water concentration levels during all processing operations. Signals from the control/display unit 44 provide the recorder portion with a continuous indication of the quality of the processed effluent.

Figure 3:
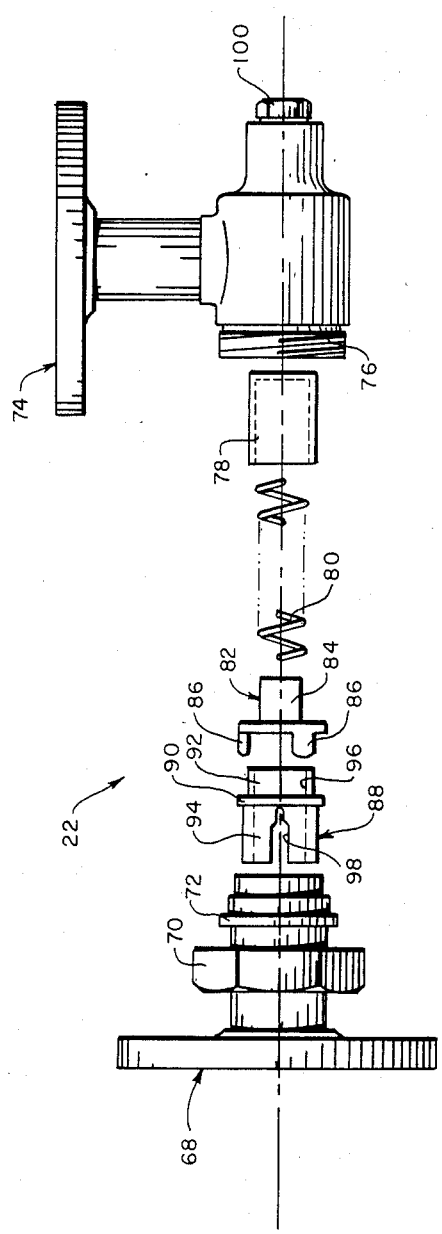
FIG. 3 is an exploded view of the oil/water disperser device of FIG. 1 according to the present invention.

An oil/water disperser device 22 suitable for use with the present invention is shown in detail in FIG. 3. It comprises a flanged inlet body 68, a locknut 70 slidably mounted to the flanged inlet body 68 and restrained by a locknut collar 72. The oil/water disperser device 22 also comprises a flanged outlet body 74 having a threaded portion 76 for operatively mounting to the flanged inlet body 68, via the locknut 70. Referring again briefly to FIG. 1, the flanged inlet body 68 would be connected to the effluent pipe section 20, and the flanged outlet body 74 would be connected to the effluent pipe section 24. It should also be mentioned, that both flanged body portions are bronze castings. The inner workings of the oil/water disperser device 22 include a spring cup guide 78, a spring 80, a relief cap 82 having a solid insert portion 84 and a plurality of tabs 86, and a plunger 88. The plunger 88 further includes a collar 90 separating a front portion 92 and a back portion 94. As illustrated in FIG. 3, plural tabs 86 are located on relief cap 82 to be received around front portion 92 of plunger 88. The plunger further includes a bore 96 configured axially in the plunger 88, and a flow-actuated variable orifice 98 configured cross-axially in the back portion 94 of the plunger 88. The flanged outlet body 74 further comprises a spring tension bolt 100 threadedly connected thereto to allow adjustment of the spring 80 via the spring cup guide 78. This, in turn, allows adjustment of the amplitude of the oscillatory action of the plunger 88 thereby controlling the opening of the flow-actuated variable orifice 98. The maximum amplitude of the oscillatory action would be as shown in FIG. 3, from the collar 90, which acts as a stop against the front of the flanged inlet body 68 out to the end of the back portion 94.

As shown, and connected via the locknut 70 and the threaded portion 76, the plunger 88 is spring loaded and the flow-actuated variable orifice 98 coacts with the processed effluent flow to oscillate in and out against the spring load of the spring 80 to provide a flow-actuated variable orifice type of shearing operation, which provides a uniform distribution of oil droplets. The plunger 88 is made from a polyethylene type of material. It was found that the polyethylene type of material is not as susceptible to galling and abrasion from the oscillating action as would occur, for example, with a bronze type plunger.

To those skilled in the art, many modifications and variations of the present invention are possible in light of the above teachings. It is therefore to be understood that the present invention can be practiced otherwise than as specifically described herein and still be within the spirit and scope of the appended claims.

What is claimed is:

1. A system for processing oil-contaminated ship bilge water for assured overboard discharge of effluent having an oil concentration only below a predetermined level, comprising:
- means processing bilge water for separating oil therefrom and expelling an effluent containing a reduced concentration of oil;
- means dispersing oil remaining in the expelled effluent into small droplets uniformly distributed throughout the effluent;
- means for extracting samples of the oil dispersed expelled effluent at regular time intervals as representative of the oil concentration therein;
- means for optically examining the samples to determine concentration of oil remaining in the expelled effluent;
- means providing electrical signals indicative of the oil in water concentration of the samples of expelled effluent;
- an effluent distributing valve unit; and,
- means processing the electrical signal for controlling the effluent distributing valve unit for directing effluent overboard when the oil concentration therein is below a predetermined level and back into the ship's bilge for further processing when the oil concentration is above the predetermined level.

2. The invention according to claim 1 further including valve means for manually directing effluent from the line leading to the ship's bilge into a holding tank.

3. A system for processing oil-contaminated ship bilge water and discharging an effluent overboard only when the oil concentration is below a predetermined concentration, comprising:
- means separating oil from the bilge water and expelling an effluent containing a reduced concentration of oil;
- disperser means for uniformly distributing any oil still present in the expelled effluent into small droplets;
- means repeatedly extracting samples of the expelled effluent having uniformly distributed oil droplets;
- means passing light through the samples and measuring the ratio of light passed directly therethrough to light scattered by oil droplets therein;
- means providing electrical signals corresponding to the light ratios;
- an effluent distributing valve unit, and,
- means processing the electrical signals for operating the distributing valve unit for directing overboard discharge of effluent when the oil concentration therein is below a predetermined level and back into the ship's bilge when the oil concentration is above a predetermined level.

4. The invention according to claim 3 including additional valve means which upon manual manipulation directs effluent having an oil concentration above a predetermined level into a holding tank.

* * * * *